United States Patent [19]

He

[11] Patent Number: 5,539,634
[45] Date of Patent: Jul. 23, 1996

[54] SHEETMAKING SYSTEM IDENTIFICATION USING SYNTHETIC MEASUREMENT PRODUCED FROM REDUNDANT NOISY MEASUREMENTS

[75] Inventor: George X. He, Menlo Park, Calif.

[73] Assignee: Measurex Corporation, Cupertino, Calif.

[21] Appl. No.: 115,599

[22] Filed: Sep. 3, 1993

[51] Int. Cl.[6] .................................................. G06F 19/00
[52] U.S. Cl. ...................... 364/158; 364/471.03; 162/262
[58] Field of Search ..................................... 364/158, 159, 364/160, 468, 469, 471, 473, 551.01; 73/159, 160; 162/198, 162

[56] References Cited

U.S. PATENT DOCUMENTS

| | | | |
|---|---|---|---|
| 3,612,839 | 10/1971 | DeWitt et al. | 364/469 |
| 3,936,665 | 2/1976 | Donoghue | 364/469 |
| 4,451,878 | 5/1984 | Shigemasa | 364/159 |
| 4,786,817 | 11/1988 | Boissevain et al. | 250/571 |
| 4,855,658 | 8/1989 | Moon | 364/469 |
| 4,903,528 | 2/1990 | Balakrishnan et al. | 73/159 |
| 4,921,574 | 5/1990 | Hu | 162/198 |
| 4,939,929 | 7/1990 | Östman | 364/471 |
| 4,947,684 | 8/1990 | Balakrishnan | 73/159 |
| 4,965,736 | 10/1990 | Balakrishnan | 364/469 |
| 5,122,963 | 6/1992 | Chen | 364/471 |
| 5,233,542 | 8/1993 | Höhner et al. | 364/187 |

Primary Examiner—Paul P. Gordon
Assistant Examiner—Brian C. Oakes
Attorney, Agent, or Firm—Burns, Doane, Swecker & Mathis

[57] ABSTRACT

In a continuous sheetmaking process, a synthetic measurement is constructed having a higher signal-to-noise ratio than that of each original measurement in situations where more than one (redundant) measurements are available. The input-output dynamic characteristics of each measurement are assumed to be identical except for a gain factor. Using the synthetic measurement, system parameters can be identified in less time with fewer input disturbances. The invention is especially advantageous for application to processes that are expensive to disturb and in which the noise amplitude is high compared to the permissible amplitude of the put disturbance. The signal-to-noise enhanced time-series response measurement may be produced by selecting a time series response measurement that exhibits a greatest magnitude. Alternatively, it may be produced by averaging in the cross-direction a plurality of time series response measurements. Preferably, the enhanced signal-to-noise ratio time-series response measurement is produced, in appropriate circumstances, by taking the root mean square of a plurality of time-series response measurements in the cross-direction. The root-mean-square or average calculation can be conducted at each sample interval such that only the synthetic measurement series needs to be collected in storage but not the matrix of all original measurements.

1 Claim, 2 Drawing Sheets

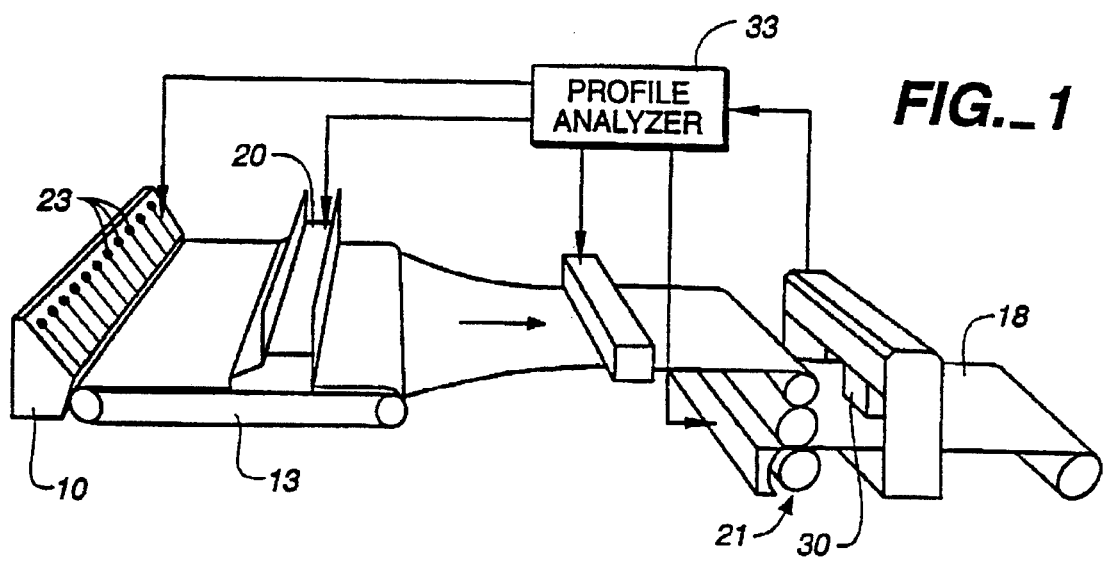
FIG._1
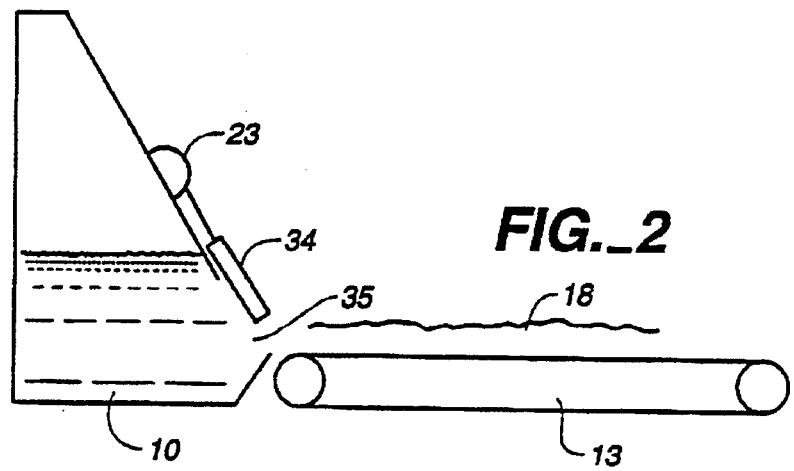
FIG._2
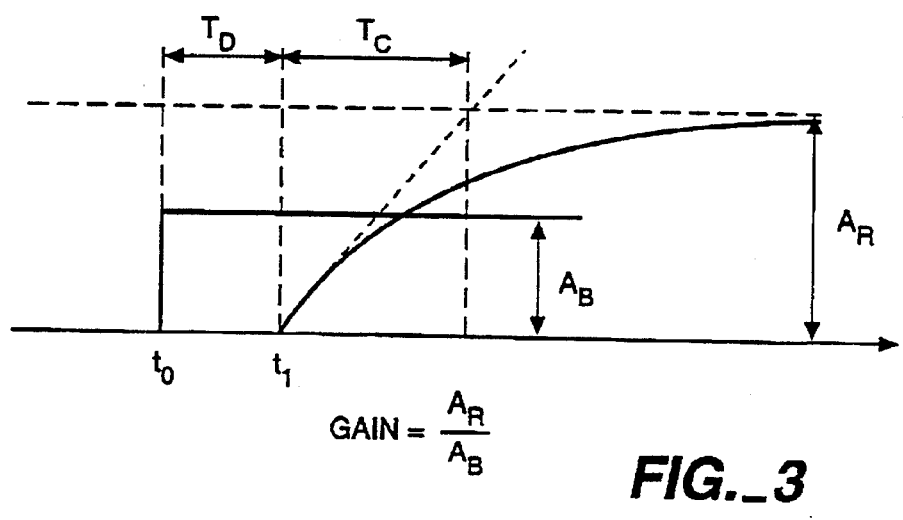
$$\text{GAIN} = \frac{A_R}{A_B}$$
FIG._3

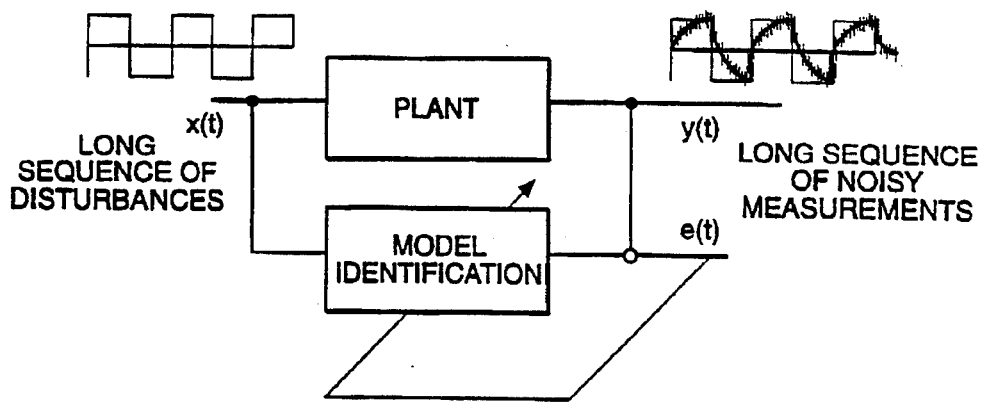
FIG._4
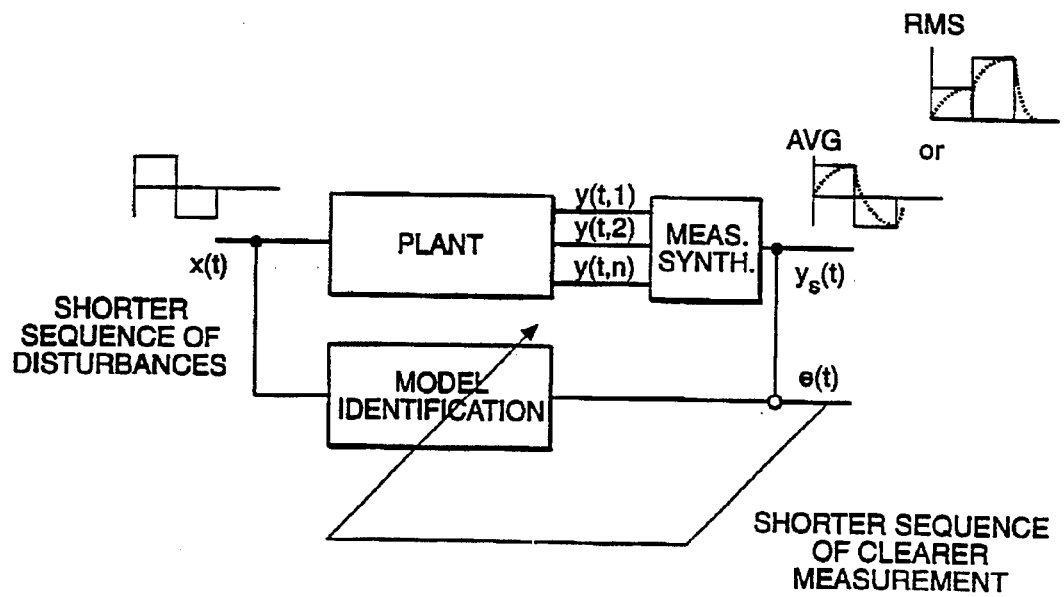
FIG._5

5,539,634

SHEETMAKING SYSTEM IDENTIFICATION USING SYNTHETIC MEASUREMENT PRODUCED FROM REDUNDANT NOISY MEASUREMENTS

BACKGROUND OF THE INVENTION

1. Related Applications

The subject matter of the present application is related to U.S. patent application Ser. No. 07/901,044 filed Jun. 22, 1992 entitled Automatic Cross-Directional Controls Zone Alignment for Sheetmaking Systems now U.S. Pat. No. 5,400,258 and U.S. patent application Ser. No. 08/115,598 filed on even date herewith entitled Self-System Parameter Identification for Systems with Pure Time-Delay, both incorporated herein by reference.

2. Field of the Invention

The present invention relates to system identification of a cross-directional control system of a type used, for example, in sheetmaking process. In particular, the invention relates to techniques for increasing the signal-to-noise ratio of measurements used in identification of such systems.

3. State of the Art

In sheetmaking processes, on-line quality measurements and controls are used to control the quality of the product. In modem automated papermaking machines, for example, continuous paper webs, sometimes measuring as much as 400 inches across, can be produced at rate of up to 100 feet per second. To control the quality of the paper manufactured at such rates and to reduce the quantity of finished product that must be rejected if there are upsets in the manufacturing processes, properties of the paper web must be measured and adjusted while the machines are operating.

Referring to FIGS. 1 and 2, in a papermaking process, a slurry of paper fibers and water mixture (or stock) is fed into a tank 10 called a "headbox", and the slurry then flows continuously through an opening 35 defined by a "slice lip" 34. The slurry is deposited onto a continuous conveyor belt, or "wire" 13. The wire moves in a direction away from the headbox. The slurry thus forms a continuous mat 18 on the wire. The mat of paper slurry drains some of its water content as it is being transported by the wire and becomes a sheet that is then pressed by rollers 21 to remove additional moisture from the sheet. The "basis weight" (mass per unit area) or other property of the sheet is then measured using a sensor, typically a scanning sensor 30 as shown in FIG. 1.

The vertical position of the slice lip is related to the size of the feed opening and hence to the amount of slurry deposited on the wire and ultimately to the basis weight of the sheet. The vertical position of the slice lip is controlled by a plurality of actuators 23 connected to the slice lip and to the headbox. Using information from a sensor, the actuators may be controlled to obtain the desired basis weight of the sheet.

Machines which produce webs of sheet material such as paper, plastic and aluminum, face process control problems in producing webs which satisfy specifications for the given sheet material. Web specifications commonly include ranges for characteristics of the web including thickness, moisture content, weight per unit area, and the like. Quality control is complicated since the specified characteristics vary in both the machine direction (MD), or direction of movement of the web through the machine, and in the machine cross direction (CD), or laterally across the web.

The MD variations are generally affected by factors that impact the entire width of the web, such as machine speed, the source of base material being formed into a web by the machine, supplies of working media like steam, and similar factors. CD variations, represented by profiles or profound signals, are normally controlled by arrays of actuation cells distributed across the width of the machine. On paper making machines, the CD actuation cells include basis weight actuators which control the slice of a headbox, steam shower nozzles, infrared heaters which control CD moisture variations, and other known devices.

To maintain the CD quality profile of the sheet with CD actuators, it is important in know the effect of each actuator unit's adjustment. This effect has two aspects, namely spatial effect and time effect. The spatial effect is normally characterized by mapping and spatial response. Mapping describes the alignment of each actuator unit to its affected portion of measured profile. Spatial response describes the pattern of the profile change due to each actuator adjustment. The time effect refers to the relation between the adjustments of an actuator and the changes of its corresponding portion of the profile in terms of their dynamic evolution over time. It is characterized as dynamic response. This invention relates to a method of identifying the dynamic response of CD control actuators.

As described in U.S. patent application Ser. No. 07/901,044, an automated tool may be used for identifying mapping and spatial response through a bump test. The same bump test result may be used to identify dynamic response of the CD control actuators. The dynamic response may be parameterizod as a time delay, a time constant, and a process gain.

A typical response to a bump excitation is shown in FIG. 3. If the bump is applied at time $t_0$, then some time later at time $t_1$ the measured sheet property will begin to change at some rate and will continue to change at a rate that gradually decreases until the system reaches a steady state condition. The amount of change of the sheet property, i.e., the amplitude of the response, $A_R$, divided by the amplitude of the bump excitation, $A_B$, is defined as the process gain. The time $t_1 - t_0$ is defined as the delay of the system, $T_D$; and the time at which the system would reach steady state if the measured sheet property changed at a non-decreasing rate is defined as the time constant of the system, $T_C$. For a time-invariant, first-order linear system, the foregoing parameters completely describe the system's behavior.

Thus, given a step response of a linear system, system parameters can be identified, for example, using a Least-Square (LS) algorithm, with little difficulty. However, noise in the response measurement, over a short transient response can be fatal to the identification result. Hence, multiple step disturbances, rather than one or two, and thus a longer response measurement time, may be required to obtain an acceptable identification result.

The foregoing situation is illustrated in FIG. 4. A long sequence of disturbances x(t) is applied to a plant. The plant may be, for example, a sheetmaking system subject to considerable process noise. The output of the plant is measured, producing a long sequence of noisy measurements y(t). The disturbances x(t) are also input to a model identification processor, which estimates the plant output. The estimated plant output is compared to the measured plant output y(b) to produce an error signal e(t), which is used to adjust the model. As the signal-to-noise ratio of the measurements decreases the length of time required for successful system identification generally increases.

In determining mapping and spatial response, cross-directional information is vitally important. In determining system parameters, on the other hand, such as time delay, time constant and process gain, cross-directional measurements through a transient response time include redundant information. Since all the actuators of the cross-direction are substantially identical and have substantially identical characteristics, each actuator is assumed to exhibit substantially the same time delay, time constant and gain.

The present invention takes advantage of the redundancy of redundant noisy measurements to produce a synthetic measurement having a higher signal-to-noise ratio that may be used to perform system identification a relatively shorter period of time, within one or two step response times.

SUMMARY OF THE INVENTION

The present invention, generally speaking, provides for the construction, in a dynamic sheetmaking process, of a synthetic measurement having a higher signal-to-noise ratio than that of each original measurement in situations where more than one (redundant) measurements are available. The input-output dynamic properties of each measurement are assumed to be identical except for a gain factor. Using the synthetic measurement, system parameters can be identified in less time with fewer input disturbances. The invention is especially advantageous for application to processes that are expensive to disturb and in which the noise amplitude is considerably high compared to the permissible amplitude of the input disturbance.

More particularly, in accordance with a preferred embodiment of the invention dynamic characteristics of a cross-directional control system having a plurality of substantially identical actuators arrayed in the cross-direction are determined by applying to the actuators respective excitation signals of equal magnitudes, collecting a profile made up of a multiplicity of measurements at different locations in the cross-direction, aggregating the multiplicity of measurements to produce a datum of a time-series response measurement; storing the datum, and repeating the collecting, aggregating and storing steps over a period of time of a response of the control system to the excitation signals. The resulting time-series response measurement has a signal-to-noise ratio substantially greater than would a time-series response measurement at any cross-direction location. Aggregating is preferably performed by forming the corrected root-mean-square of the multiplicity of measurements in a profile. Forming the corrected root-mean-square requires a noise estimate to be obtained. Therefore, prior to applying any excitation signal, a noise profile is collected and aggregated to produce a noise estimate. That estimate is refined by collecting and aggregating further noise profiles and updating the previous noise estimate.

BRIEF DESCRIPTION OF THE DRAWINGS

The present invention may be further understood from the following written description in conjunction with the appended drawings. In the drawings:

FIG. 1 is a generally schematic view of a typical papermaking system;

FIG. 2 schematically shows a side view of a feedbox for use with the papermaking system of FIG. 1;

FIG. 3 is a waveform diagram identifying certain system parameters of interest in a dynamic process;

FIG. 4 is a block diagram illustrating a system identification process using a long sequence noisy measurements; and FIG. 5 is a block diagram illustrating system identification using a shorter sequence of clearer, synthetic measurements in accordance with the present invention.

DETAILED DESCRIPTION OF THE PREFERRED EMBODIMENTS

For purposes of the following description, passing familiarity with conventional systems identification techniques is assumed. Briefly, system identification is a process in which input and corresponding output signals of a system are used to estimate dynamic characteristics of the system. Further, details concerning system identification as applied to a sheetmaking system incorporating a pure time delay may be found in co-pending U.S. application Ser. No. 08/115,598. System identification is treated at length in Ljung and Soderstrom: Theory and Practice of Recursive Identification (MIT Press, Cambridge, Mass., 1983).

The invention may be applied to advantage in papermaking systems, sheetmaking systems generally, and in other cross-directional control systems. For purposes of description, however, the invention will be described in the context of a sheetmaking system such as a papermaking system.

In such a system, automatic tuning, whereby process dynamic parameters are identified, nay be performed using data obtained from a "bump test" in which a disturbance, is applied to the system and the system output is measured, for example, by performing repeated scans across the width of the sheet using a scanning head as in FIG. 1. As repeated scans are performed, there is accumulated a two-dimensional matrix of measurement data where one of the dimensions is time, t, and the other dimension is a cross-direction spatial index, i. In the presently-described method, this two-dimensional matrix of measurement data is used to produce a one-dimensional matrix (extending in the time direction only) of measurement data that has a greater signal-to-noise ratio than any one-dimensional sub-matrix of the two-dimensional matrix taken alone. As compared to the prior art (FIG. 4), the present method allows a shorter sequence of disturbances to be used in order to produce a shorter sequence of clearer measurements as shown in FIG. 5. A measurement synthesis unit, using different measurement synthesis techniques (such as averaging or RMS) produces from n cross-directional measurements a single synthetic output measurement $y_s(t)$ having an enhanced signal-to-noise ratio.

In accordance with a first-order linear model, the time-varying output at different discrete measurement points i in the cross-direction output, $y(t,i)$, of a sheetmaking (or other) system may be modelled in terms of its input signal, $x(t)$, as:

$$y(t,i) = a_1 y(t-1,i) + \ldots + a_n y(t-n,i) \quad (1)$$

$$+ p(i)[b_1 x(t-d) + \ldots + b_m x(t-d-m+1)] \quad (2)$$

$$+ v(t,i), i+1, \ldots N \quad (3)$$

where $a_1, a_2, \ldots$ and $b_1, b_2, \ldots$ are process model parameters, d represents an unknown time-delay, p(i) n;presents the process gain at the different discrete measurement points in the cross-direction, and where $v(t,i)$ is assumed to be Gaussian and white noise with zero mean and variance $\sigma_v$ for all i. It is the gain p(i) that makes one measurement different from another. From a theoretical point of view, all of the measurements $y(t,i)$ except one are redundant for the purpose of identifying the unknown parameters.

The redundant measurements can be operated upon or combined in many different ways to construct a synthetic measurement that yields a higher signal-to-noise ratio. The simplest approach, if the process gain p(i) varies among the different discrete measurement points in the cross-direction, is to simply select as the output signal y(t) a measurement (or rather series of measurements) taken at a point in the cross-direction at which the gain is greatest:

$$y_m(t) = y(t,k) = y(t) \quad (4)$$

where k is determined by $p(k) = \max_{1 \geq i \geq N} P(i)$. (Without losing generality, it is assumed that $p(k)=1$.) The maximum measurement is a single (non-synthetic) measurement that yields the maximum signal-to-noise ratio among all single measurements, y(t,i). This approach requires the knowledge of point in CD at which the gain is high. Otherwise, the two dimensional array of all point measurements needs to be stored.

The signal-to-noise ratio may be increased beyond the maximum signal-to-noise ratio among all single measurements by producing a synthetic measurement. One method is to average together the measurements at all of the discrete measurement points in the cross-direction, as follows:

$$y_a(t) = Y_a \sum_{i=1}^{N} y(t,i)/N \quad (5)$$

$$Y_a = 1 / \left( \sum_{i=1}^{N} p(i)/N \right) = 1/\text{AVG}_p \quad (6)$$

where $Y_a$ is a normalization factor accounting for possible different gains p(i).

By taking the average of all measurements in the cross-direction, the respective noise components, assumed to be uncorrelated, tend to cancel out. The average measurement may be shown to have the same mean value as that of the maximum measurement while yielding a signal-to-noise ratio that is $$F_a = \sqrt{N}/|Y_a| \quad (7)$$

times that of the maximum measurement. A larger number of measurements will lead to a higher signal-to-noise ratio, when the input to the system remains the same. Note that this approach requires only a one dimensional army to be stored during the dam collection. In other words, after one scan of a profile of measurements at different cross-directional locations, only the average of the profile is stored as $y_i(t)$ at the time t.

An even more robust measurement may be constructed by taking Corrected Root-Mean-Square (CRMS) of measurement at all of the discrete measurement points, as follows:

$$y_r(t) = Y_r [RMS_y^2(t) - \sigma_y^2]^{1/2}, \quad (8)$$

$$RMS_y^2(t) = \sum_{i=1}^{N} y(t,i)^2/N \quad (9)$$

$$Y_r = 1/\sqrt{\sum_{i=1}^{N} p(i)^2/N} \quad (10)$$

The CRMS measurement has the same mean value as the absolute value of the maximum measurement while yields a signal-to-noise ratio that is $$F_r = \sqrt{N}/Y_r \quad (11)$$

times that of the maximum measurement.

Note that, for $N \geq 2$, $$F_r/F_a = RMS_p/|\text{AVG}_p| \geq \sqrt{N/2} \geq 1, \quad (12)$$

which indicates superiority of the CRMS measurement over the average measurement in terms of signal-to-noise ratio. The CRMS measurement yields the highest signal-to-noise ratio and should be used for applications where sign of the measurement is not varying or is known. The signal-to-noise ratio increases with the number of measurements available in power of ½. Unlike averaging, in the RMS technique, since sign information is obscured, separate noise components, instead of tending to cancel, accumulate. A correction must therefore be made, represented by the minuend term $\sigma_y^2$. In the CRMS measurement (9), $\sigma_y$ is the variance of each single measurement y(t,i). It is a function of the variance $\sigma_v$, of each process noise measurement $v_i(t,i)$. For a time-invariant system and steady process noise, $\sigma_y$ can be approximated by a RMS value of the measurements during a period of time with zero input, i.e., $$\sigma_Y^2 = (1/N) \sum_{i=1}^{N} (1/T) \sum_{t=1}^{T} [y(t,i)|_{x(t)=0}]^2 = \quad (13)$$

$$(1/T) \sum_{t=1}^{T} \sum_{i=1}^{N} [y(t,i)|_{x(t)=0}]^2/N$$

In other words, in the CRMS measurement technique, prior to applying a disturbing input signal and collecting a series of measurement profiles, a series of noise profiles are collected without any disturbing input being applied. The mean square noise value is calculated across each profile. For each noise profile collected, a noise estimate is updated by computing the time average of the mean square noise values. Then, as the RMS measurement is computed, the RMS value is corrected to account for the process estimate.

As in calculation of the average measurement, this approach only requires a one dimensional array of dam to be stored.

In the average measurement and the corrected RMS measurement, the scaling factors $Y_a$ and $Y_r$ depends on p(i), which are usually unknown. With the exception of the overall input-output gain, these scaling factors will not affect the system parameter identification ($a_i$, $b_i$, and d). Therefore, these scaling factors p(i) can be estimate, d afterwards from the system response measurements and then used to scale the input-output gain identification. The estimation can be performed as:

$$Y_a \cong \left[ (1/n) \sum_{i=1}^{N} y(t,i)|_{t=T} \right] \quad (14)$$

and $$1/Y_r \cong \sqrt{(1/N) \sum_{i=1}^{N} [y(t,i)|_{t+T}]^2 - \sigma_y^2} \quad (15)$$

where T is a time when step responses reached or got close to steady state.

In most common sheet production process Cross-Direction (CD) control systems, a greater number of measurements is performed during each scan than the number of corresponding actuators. Therefore, multiple measurements are affected and dominated by a single actuator, although the gain from actuator input to measurement output may not be the same for all of such measurements. The dynamic characteristics of each actuator's response can be approximated as a first order dynamic system. In such case, the system model, provided that process noise in each measurement zone is independent from the other (for a first order system), can be written as:

$$y(t,i) = ay(t-1,i) + bp(i)x(t-d) + v(t,i) \qquad (16)$$

with i=1,2, ..., N. In other words, $a_2, a_3, \ldots$ and $b_2, b_3, \ldots$ may be taken to be zero. Theoretically, the variance $\sigma_y$ of all the measurements is $$\sigma_y^2 = \sigma_v^2/(1-a^2) \qquad (17)$$

where $\sigma_v$ is the variance of the process noise v(t,i). In practice, $\sigma_y$ is estimated according to equation (13). Then the CRMS measurement can be constructed according to equations (8–10).

A generalized version of the recursive Least Square algorithm can be used for parameter (a, b and d) identification as described in greater detail in U.S. application Ser. No. 08/155,598.

The foregoing has described the principles, preferred embodiments and modes of operation of the present invention. However, the invention should not be construed as limited to the particular embodiments discussed. Instead, the above described embodiments should be regarded illustrative rather than restrictive, and it should be appreciated that variations may be made in those embodiments by workers skilled in the art without departing from the scope of the present invention as defined by the following claims.

What is claimed:

1. For use in a sheetmaking process, a method of determining dynamic characteristics of a cross-directional control system having a plurality of substantially identical actuators arrayed in the cross-direction, the method comprising the steps of:

in the absence of any excitation signal,
   (1) collecting a profile made up of a multiplicity of measurements at different locations in the cross-direction;
   (2) aggregating said multiplicity of measurements to produce a noise estimate;
   (3) collecting a further profile;
   (4) using said further profile, updating said noise estimate;
   (5) repeating steps (3) and (4) until said noise estimate does not change more than a specified amount;

thereafter,
   (6) applying to a plurality of the actuators respective excitation signals of substantially equal magnitudes;
   (7) collecting a profile made up of measurements at a multiplicity of different locations in the cross-direction;
   (8) aggregating said multiplicity of measurements by using said noise estimate to calculate the Corrected Root-Mean-Square of said multiplicity of measurements to produce a single value;
   (9) storing said single value; and
   (10) repeating steps (7), (8) and (9) over a period of time of a response of the cross-directional control system to the excitation signals, to produce a resulting time-series.

* * * * *